United States Patent [19]

Schadt et al.

[11] 4,180,475
[45] Dec. 25, 1979

[54] LIQUID CRYSTAL MIXTURES

[75] Inventors: Martin Schadt, Seltisberg; Hanspeter Scherrer, Therwil; Arthur Boller, Binningen, all of Switzerland

[73] Assignee: Hoffmann—La Roche Inc. Nutley, N.J.

[21] Appl. No.: 769,999

[22] Filed: Feb. 18, 1977

[30] Foreign Application Priority Data

Feb. 26, 1976 [CH] Switzerland .................. 2372/76
Jul. 9, 1976 [CH] Switzerland .................. 8832/76
Dec. 20, 1976 [CH] Switzerland .................. 15995/76

[51] Int. Cl.² .................. C09K 3/34; G02F 1/13
[52] U.S. Cl. .................. 252/299; 252/408; 350/350
[58] Field of Search .................. 252/299, 408; 350/160 LC, 350

[56] References Cited

U.S. PATENT DOCUMENTS

| | | | |
|---|---|---|---|
| 3,815,972 | 6/1974 | Hsieh | 252/408 |
| 3,826,757 | 7/1974 | Wong | 252/408 |
| 3,923,857 | 12/1975 | Boller et al. | 252/299 |
| 3,927,064 | 12/1975 | Doller et al. | 252/299 |
| 3,927,066 | 12/1975 | Scherrer et al. | 252/299 |
| 3,947,375 | 3/1976 | Gray et al. | 252/299 |
| 3,951,845 | 4/1976 | Cole, Jr. | 252/299 |
| 3,960,749 | 6/1976 | Fergason | 252/299 |
| 3,972,589 | 8/1976 | Skelly et al. | 252/299 |
| 3,979,319 | 9/1976 | Fukai et al. | 252/299 |
| 3,983,049 | 9/1976 | Aftercut | 252/299 |
| 3,997,536 | 12/1976 | Boller et al. | 252/299 |
| 4,000,084 | 12/1976 | Hsieh et al. | 252/299 |
| 4,003,844 | 1/1977 | Sorkin | 252/299 |
| 4,011,173 | 3/1977 | Steinstrasser | 252/299 |
| 4,038,200 | 7/1977 | Jones et al. | 252/299 |
| 4,059,340 | 11/1977 | Kahn et al. | 252/299 |
| 4,062,798 | 12/1977 | Doller et al. | 252/299 |
| 4,099,856 | 7/1978 | Weissflog et al. | 252/299 |
| 4,118,335 | 10/1978 | Krause et al. | 252/299 |

FOREIGN PATENT DOCUMENTS

| | | | |
|---|---|---|---|
| 2257588 | 6/1973 | Fed. Rep. of Germany | 252/299 |
| 2454570 | 5/1975 | Fed. Rep. of Germany | 252/299 |
| 2535125 | 2/1976 | Fed. Rep. of Germany | 252/299 |
| 2548360 | 5/1977 | Fed. Rep. of Germany | 252/299 |
| 2557267 | 6/1977 | Fed. Rep. of Germany | 252/299 |
| 49-45886 | 1/1974 | Japan | 252/299 |
| 49-37884 | 8/1974 | Japan | 252/299 |
| 51-88485 | 3/1976 | Japan | 252/299 |

OTHER PUBLICATIONS

Dave, J. S., et al., J. Chem. Soc., pp. 4305–4309 (1955).

Taylor, G. N., et al., J. Appl. Phys., vol. 45, No. 10, pp. 4330–4338 (1974).

Creach, L. T., et al., J. Elect. Materials, vol. 1, pp. 350–354 (1972).

Primary Examiner—Benjamin R. Padgett
Assistant Examiner—T. S. Gron

Attorney, Agent, or Firm—Jon S. Saxe; George M. Gould; Peter R. Shearer

[57] ABSTRACT

Liquid crystal mixtures having positive anisotropy of the dielectric constants which comprise a nematogenic mixture with a clearing point above 60° C. which is doped with an organic solvent or solvent mixture with a specific resistance of at least $10^7$ Ohm.cm. as well as a dipole moment along the longitudinal axis of the molecule of less than 3.5 Debye, or with a compound of the formula

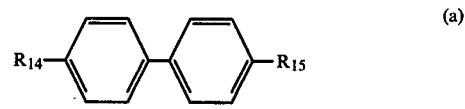

(a)

wherein $R_{14}$ and $R_{15}$ are straight-chain alkyl containing a total of not more than 14 carbon atoms or $R_{14}$ is straight-chain alkyl and $R_{15}$ is straight-chain alkoxy containing a total of not more than 8 carbon atoms, or a compound of the formula

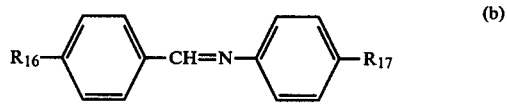

(b)

wherein $R_{16}$ and $R_{17}$ are straight-chain alkyl containing a total of not more than 6 carbon atoms, or a compound of the formula

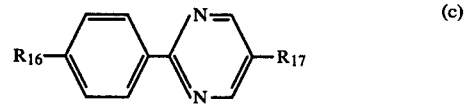

(c)

wherein $R_{16}$ and $R_{17}$ are straight-chain alkyl containing a total of not more than 6 carbon atoms, or mixtures thereof, are described.

27 Claims, No Drawings

LIQUID CRYSTAL MIXTURES

BRIEF SUMMARY OF THE INVENTION

The invention relates to liquid crystal mixtures having a positive anisotropy of the dielectric constants which comprise a nematogenic mixture with a clearing point above 60° C. which is doped with an organic solvent or solvent mixture with a specific resistance of at least $10^7$ Ohm.cm. as well as a dipole moment along the longitudinal axis of the molecule of at least 3.5 Debye, or with a compound of the formula

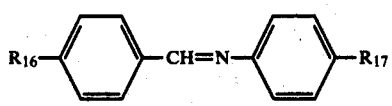
(a)

wherein $R_{14}$ and $R_{15}$ are straight-chain alkyl containing a total of not more than 14 carbon atoms or $R_{14}$ is straight-chain alkyl and $R_{15}$ is straight-chain alkoxy containing a total of not more than 8 carbon atoms, or with a compound of the formula

(b)

wherein $R_{16}$ and $R_{17}$ are straight-chain alkyl containing a total of not more than 6 carbon atoms, or with a compound of the formula

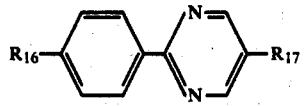
(c)

wherein $R_{16}$ and $R_{17}$ are as previously described, or mixtures thereof.

In a further aspect, the invention relates to compounds of formula (c) and electro-optical apparatuses containing the liquid crystal mixtures of the invention.

DETAILED DESCRIPTION OF THE INVENTION

The invention relates to liquid crystal mixtures. More particularly, the invention relates to liquid crystal mixtures, compounds, and processes for the preparation thereof and electro-optical apparatus containing the liquid crystal mixtures.

The liquid crystal mixtures of the invention have positive anisotropy of the dielectric constants and contain a nematogenic mixture with a clearing point above 60° C. and an organic solvent or solvent mixture with a specific resistance of at least $10^7$ Ohm.cm. as well as a dipole moment along the longitudinal axis of the molecule of less than 3.5 Debye, or a compound of the formula

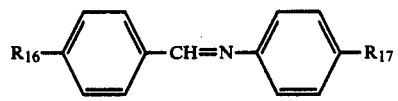
(a)

wherein $R_{14}$ and $R_{15}$ are straight-chain alkyl containing a total of not more than 14 carbon atoms or $R_{14}$ is straight-chain alkyl and $R_{15}$ is straight-chain alkoxy containing a total of not more than 8 carbon atoms, or a compound of the formula

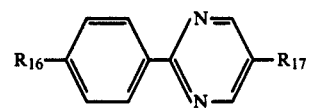
(b)

wherein $R_{16}$ and $R_{17}$ are straight-chain alkyl containing a total of not more than 6 carbon atoms, or a compound of the formula (c)

wherein $R_{16}$ and $R_{17}$ are as previously described, or mixtures thereof.

The term "liquid crystal mixture" as used in the specification relates to mixtures which have a nematic mesophase. Similarly, the term "nematogenic" relates to materials which have a nematic mesophase.

In an electrical field, liquid crystals having positive anisotropy of the dielectric constants ($\epsilon_{\parallel} > \epsilon_{\perp}$, $\epsilon_{\parallel}$ denoting the dielectric constant along the longitudinal axis of the molecule and $\epsilon_{\perp}$ denoting the dielectric constant perpendicular thereto) orientate themselves with the direction of their largest dielectric constant (that is, with their longitudinal axes) parallel to the field direction. This effect is used, inter alia, in the interaction between embedded molecules and the liquid crystalline molecules (guest-host interaction) described by J. H. Heilmeier and L. A. Zanoni [Applied Physics Letters, 13, 91 (1968)]. Another interesting application of the dielectric field orientation exists in the rotation cell discovered by M. Schadt and W. Helfrich [Applied Physics Letters 18 (1971)] and in the Kerr cell described in Molecular Crystals and Liquid Crystals 17, 355 (1972).

The rotation cell mentioned earlier is essentially a condenser having transparent electrodes, the dielectric of which is formed from a nematic medium with $\epsilon_{\parallel} > \epsilon_{\perp}$. The longitudinal molecular axes of the liquid crystal are arranged in twisted form between the condenser plates in the fieldless state. The twisting structure is determined by the given wall orientation of the molecules. Upon the application of an electrical potential to the condenser plates, the molecules adjust themselves with their longitudinal axes in the field direction, that is, perpendicular to the plate surface, whereby linearly polarized light is no longer rotated in the dielectric, that is, the liquid crystal becomes uniaxially perpendicular to the surface of the plates. This effect is reversible and can be used to control electrically the optical transmissivity of the condenser.

In such a rotation cell it is, inter alia, desirable to use compounds or mixtures which have a low threshold and operating potential, this being important, for example, when using a rotation cell display in clocks.

A great disadvantage of liquid crystal mixtures used today for many applications lies in the fact that they have operating potentials in rotation cell displays which are too high. This property rules out, for example, the direct control of wristwatch displays by a single monocell. A further result of high operating potentials is the associated higher residual currents which flow in the display, resulting, in turn, in a higher power dissipation and thus a shorter battery life. Increased residual currents also have a disadvantageous effect upon the life of displays since they accelerate electrochemical reactions which can occur on the display electrodes.

Another disadvantageous property of displays based on a field effect such as, for example, the rotation cell described hereinbefore, is the relatively long electro-optical response times which are essentially attributable to the fact that liquid crystal mixtures used today have high viscosities. Since the viscosity of a liquid increases exponentially with decreasing temperature, this can lead, for example, to response times of wristwatch displays increasing at low temperatures in such a way that a second hand is ruled out. The high viscosities of today's liquid crystal mixtures also limit the applicability thereof to displaying rapidly altering information, for example, in matrix displays for displaying pictures or in rapid electro-optical seals.

In accordance with the present invention, it has now been established that the aforementioned disadvantages of liquid crystal mixtures can be substantially reduced when the nematogenic mixtures, which are to be used in the displays, are doped with an organic solvent or solvent mixture with a specific resistance of at least $10^7$ Ohm.cm. as well as a dipole moment along the longitudinal axis of the molecule of less than 3.5 Debye, or with a compound of formula (a), (b) or (c) hereinbefore or a mixture thereof; that is to say when about 0.5% to about 15% of an organic solvent or solvent mixture described above or up to about 40% of a compound of formula (a), (b) or (c) or a mixture thereof is added to the nematogenic mixtures.

For appropriate reasons, the solvent or solvent mixture used must have a high specific resistance, namely of at least $10^7$ Ohm.cm., preferably of at least $10^9$ Ohm.cm. Moreover, the dipole moment along the longitudinal axis of the molecule must be less than 3.5 Debye. In order to keep evaporation of the solvent low at high temperatures and/or at low pressures, the boiling points of the solvents or solvent mixtures and their heats of vaporization should be as high as possible. Solvents and solvent mixtures having a boiling point at atmospheric pressure of above 100° C. are preferably utilized. Furthermore, the viscosities of the solvents or solvent mixtures used should be lower than those of the nematogenic mixtures used if a lowering in the viscosity of the liquid crystal mixtures is to be achieved simultaneously with the lowering of the threshold and operating potential. It will be understood that the solvent or solvent mixture used is soluble in the nematogenic mixture to be doped. Exemplary of solvents which fulfil the aforementioned criteria are: alkanes which are straight-chain or have one —CH(CH$_3$)— group and contain a total of 8-16 carbon atoms, for example, decane, octane and 2-methylnonane; alkenes which are straight-chain or have one —CH(CH$_3$)— group and contain a total of 8-16 carbon atoms, for example, trans dec-5-ene and trans oct-4-ene; alkynes which are straight-chain or have one —CH(CH$_3$)— group and contain a total of 8-16 carbon atoms, for example, dec-5-yne; alkyl halides, the alkyl radical of which is straight-chain or has one —CH(CH$_3$)— group and contains a total of 6-16 carbon atoms, for example, 1-bromohexane, 1-bromododecane and 1,6-dichlorohexane; dialkyl ethers, the alkyl radicals of which are straight-chain or have one —CH(CH$_3$)— group and each contain a total of 4-8 carbon atoms, for example, dibutyl ether, dihexyl ether, dioctyl ether and propyl heptyl ether; alkyl aldehydes, the alkyl radical of which is straight-chain or has one —CH(CH$_3$)— group and contains a total of 6-16 carbon atoms, for example, capric aldehyde and caproic aldehyde; dialkyl carbonates, the alkyl radicals of which are straight-chain or have one —CH(CH$_3$)— group and each contain a total of 2-7 carbon atoms, for example, diethyl carbonate and dibutyl carbonate; alkanecarboxylic acid alkyl esters, the alkyl radicals of which are straight-chain or have one —CH(CH$_3$)— group and together contain 6-16 carbon atoms, for example, butyric acid propyl ester, butyric acid pentyl ester and caproic acid octyl ester; dialkyl ketones, the alkyl radicals of which are straight-chain or have one —CH(CH$_3$)— group and each contain a total of 2-7 carbon atoms, for example, diethyl ketone, dihexyl ketone and methyl octyl ketone; monosubstituted or disubstituted, preferably para-disubstituted, benzene derivatives, for example, p-xylene, 1-phenylheptane, p-octylbenzoic acid methyl ester, p-hexylbenzaldehyde and the like.

Preferred solvents are alkanes, alkyl halides, dialkyl ethers, dialkyl carbonates and alkanecarboxylic acid alkyl esters as hereinbefore described and 1-phenylheptane and p-xylene. The dialkyl ethers and alkanecarboxylic acid alkyl esters are particularly preferred. Dibutyl ether, dihexyl ether, dioctyl ether, butyric acid propyl ester and butyric acid pentyl ester are the most preferred solvents.

The liquid crystal mixtures according to the invention conveniently contain from about 0.5% to about 15%, preferably about 0.5% to about 10%, of solvent or solvent mixture. Particularly preferred are liquid crystal mixtures which contain from about 3% to about 8% of solvent or solvent mixture.

Insofar as the liquid crystal mixtures provided by the present invention contain a compound of formula (a), (b) or (c) or mixtures thereof, said compounds or mixtures are conveniently present in an amount of up to about 40%, preferably in an amount of from about 7% up to about 30%, and most preferably in an amount of from about 10% up to about 25%. In the case where mixtures of an organic solvent or solvent mixture and one or more compounds of formula (a), (b) or (c) are added to the liquid crystal mixtures, this is conveniently carried out in an amount of up to about 45%, preferably in an amount of from about 10% to about 35%, and most preferably in an amount of from about 10% to about 25%. All percentages are based upon weight/weight.

The compounds of formula (a) are known. In the case where $R_{14}$ and $R_{15}$ both represent straight-chain alkyl, the total number of carbon atoms comprise no more than 14, as already mentioned. Preferred alkyl groups are those having 2 to 5 carbon atoms. Those compounds in which $R_{14}$ is alkyl of 2 or 3 carbon atoms and $R_{15}$ is alkyl of 4 or 5 carbon atoms are especially preferred.

In the case where $R_{14}$ is straight-chain alkyl and $R_{15}$ is straight-chain alkoxy, the total number of carbon atoms comprise no more than 8. Preferred compounds of this type are those in which $R_{14}$ and $R_{15}$ each have 1 to 3 carbon atoms.

The compounds of formula (b) are also known and the total number of carbon atoms in the groups $R_{16}$ and $R_{17}$ comprise no more than 6. Preferred compounds are those in which $R_{16}$ and $R_{17}$ are alkyl each containing 1 to 4 carbon atoms. An especially preferred compound is one in which $R_{16}$ is methyl and $R_{17}$ is n-butyl.

The compounds of formula (c) are novel and it will be appreciated that they also form part of the present invention.

As mentioned earlier, the total number of carbon atoms in the groups $R_{16}$ and $R_{17}$ in the compounds of formula (c) comprise no more than 6. Preferred alkyl groups in the compounds of formula (c) are those with 2 to 4 carbon atoms. The compound in which $R_{16}$ is ethyl and $R_{17}$ is n-butyl is especially preferred.

The novel compounds of formula (c) can be prepared, for example, from a p-alkylbenzamidine hydrochloride by (a) reaction under basic conditions with the enol ether aldehyde of the formula

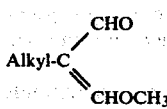

which is obtainable from a 2-alkylmalonic tetraacetal by partial acidic hydrolysis, or (b) reaction with a 2-alkylmalonic ester, conversion of the resulting 2-(4'-alkylphenyl)-4-alkyl-4,6-dihydroxypyrimidine by treatment with phosphorus oxychloride into the corresponding 2-(4'-alkylphenyl)-5-alkyl-4,6-dichloropyrimidine and reduction of the latter with hydrogen in the presence of palladium/carbon.

The nematogenic material used consists of at least two components, it is not necessary for all the compounds used as components of the nematogenic material to themselves have a nematic mesophase, that is, the nematogenic mixture can also contain non-nematogenic substances; only the resulting mixture must be nematogenic. Similarly, it is not necessary for all the compounds used as components to have a positive anisotropy of the dielectric constants. Thus, compounds with a negative anisotropy of the dielectric constants can also be admixed, and even the nematogenic mixture to be doped with solvent can have a negative anisotropy of the dielectric constants; each of the liquid crystal mixtures provided by the invention, however, must have a positive anisotropy of the dielectric constants.

It is known that the clearing point of nematogenic mixtures is lowered by the addition of solvents. Therefore, such liquid crystal mixtures are then only of particular interest if the nematogenic mixtures used have high clearing points before the doping. The preparation of nematic mixtures with high clearing points, preferably above 60° C., can be carried out according to known methods and thus will not be illustrated in further detail in the present specification.

The nematogenic mixtures utilized in the present invention preferably contain one or more compounds of the formula

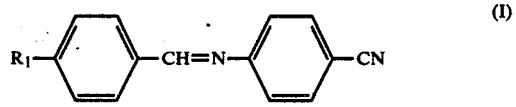

wherein $R_1$ is straight-chain alkyl containing 2 to 8 carbon atoms, straight-chain alkoxy containing 4 to 7 carbon atoms, straight-chain alkanoyloxy containing 2 to 8 carbon atoms or straight-chain alkylcarbonate containing 2 to 11 carbon atoms, and/or one or more compounds of the formula

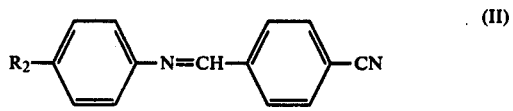

wherein $R_2$ is straight-chain alkyl containing 4 to 7 carbon atoms or straight-chain alkylcarbonate containing 2 to 11 carbon atoms, and/or one or more compounds of the formula

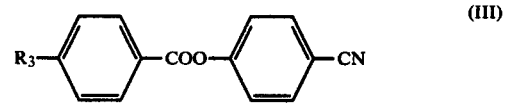

wherein $R_3$ is straight-chain alkyl containing 4 to 8 carbon atoms, straight-chain alkoxy containing 5 to 8 carbon atoms, straight-chain alkanoyloxy containing 2 to 8 carbon atoms or straight-chain alkylcarbonate containing 3 to 11 carbon atoms, and one or more compounds of the formula

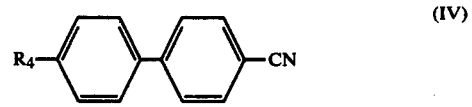

wherein $R_4$ is straight-chain alkyl containing 4 to 8 carbon atoms, straight-chain alkoxy containing 4 to 8 carbon atoms, straight-chain alkanoyloxy containing 4 to 9 carbon atoms or straight-chain alkylcarbonate containing 4 to 11 carbon atoms, and/or one or more trans-cinnamic acid esters of the formula

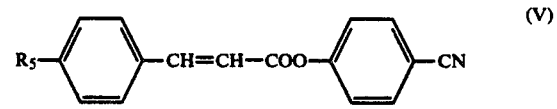

wherein $R_5$ is straight-chain alkyl containing 1 to 8 carbon atoms, and/or one or more compounds of the formula

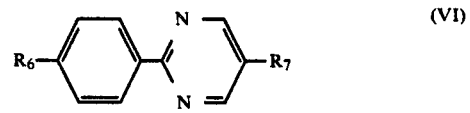

wherein one of $R_6$ and $R_7$ is cyano and the other is straight-chain alkyl containing 3 to 9 carbon atoms, straight-chain alkoxy containing 2 to 9 carbon atoms or straight-chain alkanoyloxy containing 2 to 9 carbon atoms,
and/or one or more compounds of the formula

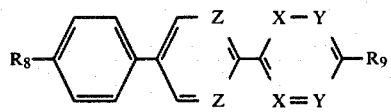 (VII)

wherein one of $R_8$ and $R_9$ is hydrogen, straight-chain alkyl containing 1 to 7 carbon atoms, straight-chain alkoxy containing 1 to 7 carbon atoms or straight-chain alkanoyloxy containing 2 to 7 carbon atoms and the other is cyano; and one of X, Y and Z is nitrogen and the other two, independently, are a CH group,
and/or one or more compounds of the formula

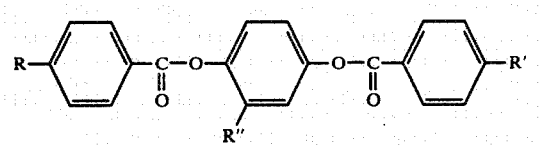 (A)

wherein R and R' are straight-chain alkyl containing 1 to 10 carbon atoms, straight-chain alkoxy containing 1 to 10 carbon atoms, straight-chain alkanoyloxy containing 2 to 11 carbon atoms or straight-chain alkylcarbonate containing 2 to 11 carbon atoms and R" is chlorine, bromine or methyl,
and/or one or more compounds of the formula

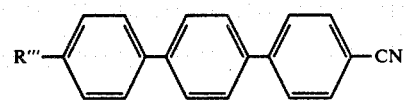 (B)

wherein R''' is straight-chain alkyl containing 3 to 8 carbon atoms.

The compounds of formula VI are new and can be prepared by dehydrating a compound of the formula

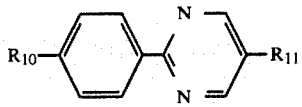 (VIII)

wherein one of $R_{10}$ and $R_{11}$ is straight-chain alkyl containing 3 to 9 carbon atoms, straight-chain alkoxy containing 2 to 9 carbon atoms or straight-chain alkanoyloxy containing 2 to 9 carbon atoms and the other is —$CONH_2$.

The dehydration of a compound of formula VIII can be carried out utilizing any suitable dehydrating agent, such as, for example, phosphorus oxychloride, phosphorus pentoxide, thionyl chloride or acetic anhydride. The dehydration can be carried out in an inert organic solvent, for example, in a hydrocarbon or halogenated hydrocarbon, if necessary in the presence of a base, such as, sodium acetate, pyridine or triethanolamine. The dehydration can, however, also be carried out in the absence of an organic solvent. Preferably, the dehydration is carried out at the reflux temperature of the mixture. The pressure is not critical, but it is advantageous to carry out the dehydration at atmospheric pressure.

The preparation of the compounds of formula VIII is illustrated in Formula Schemes 1 and 2 which follow for compounds in which one of $R_{10}$ and $R_{11}$ is straight-chain alkyl containing 3 to 9 carbon atoms. In the Formula Schemes "Alkyl" denotes a straight-chain alkyl group containing 3 to 9 carbon atoms.

Formula Scheme 1

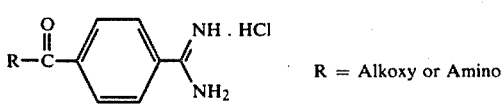

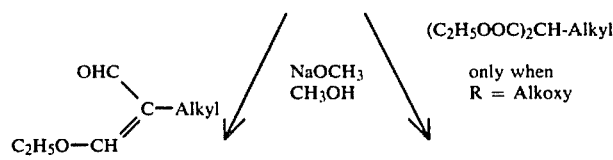

Formula Scheme 4
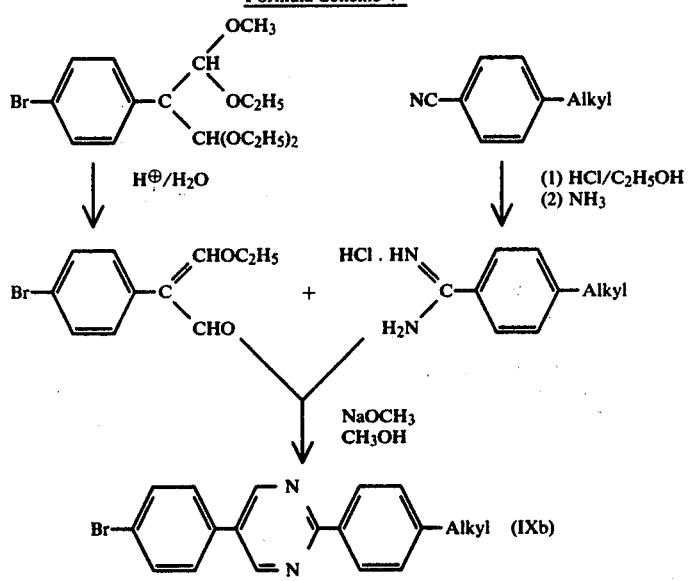
Formula Scheme 5
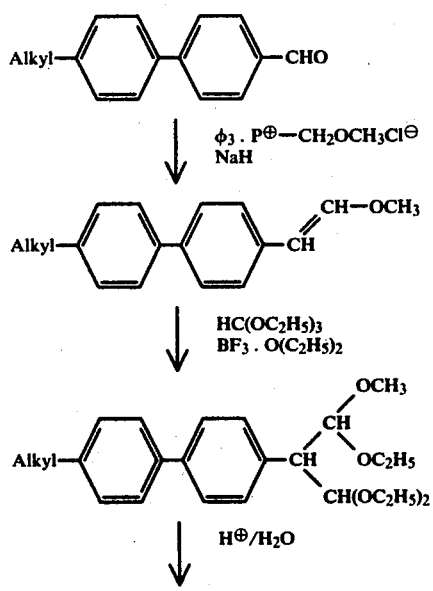
-continued
Formula Scheme 5
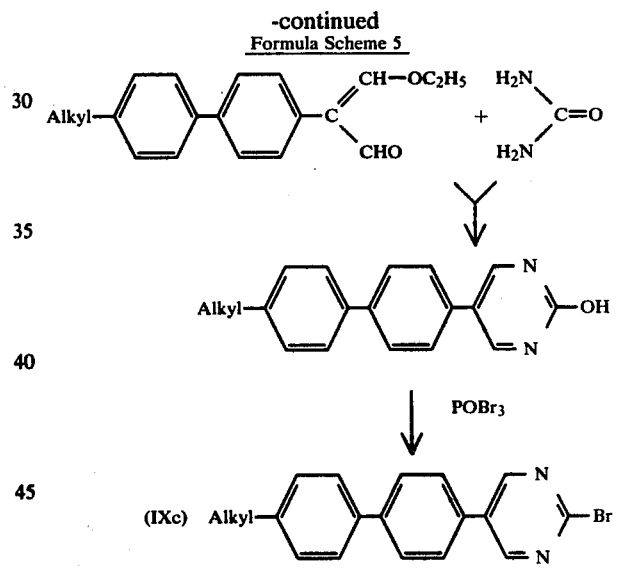
Formula Scheme 6
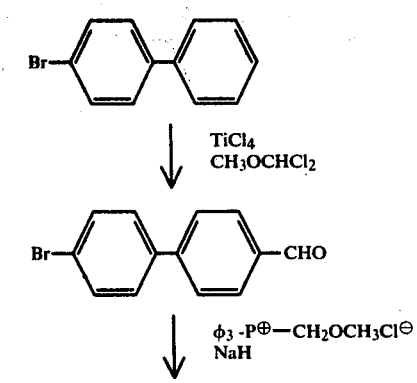

Formula Scheme 6
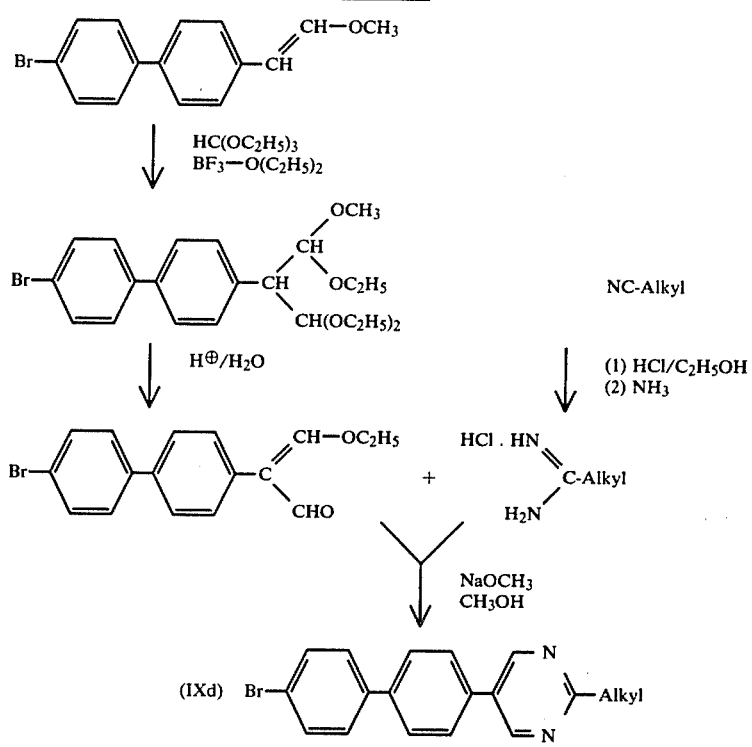
Formula Scheme 7
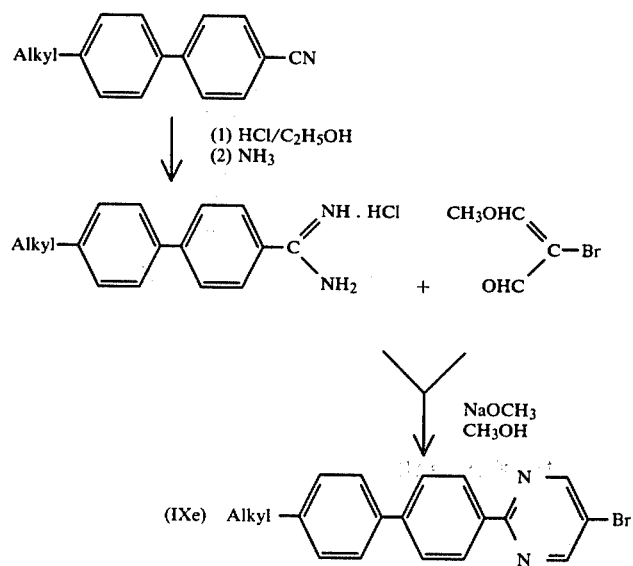
Formula Scheme 8
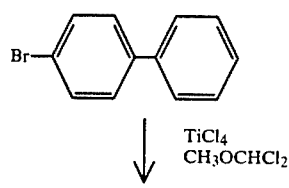

Formula Scheme 8

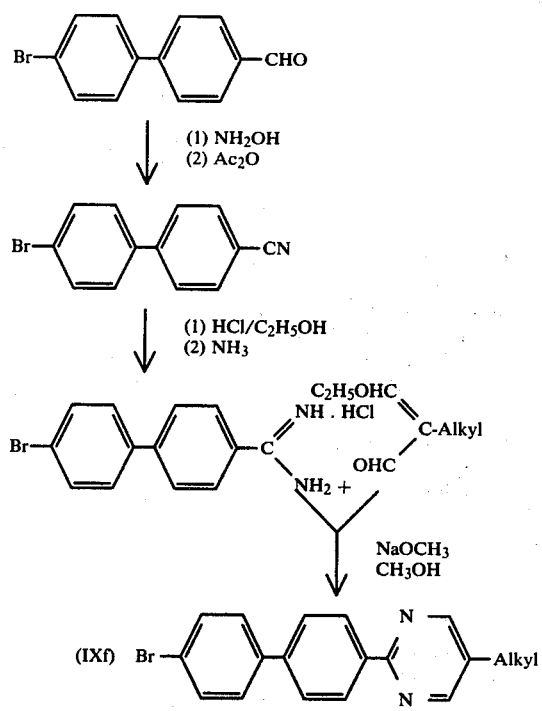

The present invention is further illustrated in Table I, wherein the physical properties of some of the liquid crystal mixtures provided by the invention are listed in comparison with the corresponding nematogenic mixtures which have not been doped:

Table I

| Mixture | M.p. (°C.) | C.p. (°C.) | Viscosity (cp) | $\epsilon_\mu$ | $\Delta\epsilon$ | fc (MHz) | V(10) (Volt) | V(90) (Volt) | Measuring temp. (°C.) |
|---|---|---|---|---|---|---|---|---|---|
| A | ~0 | 71 | 201 | 25.30 | 17.80 | 0.30 | 1.15 | 1.60 | 22 |
| A + 6% Dihexyl ether | ~0 | 50 | 108 | 21.79 | 14.01 | 1.15 | 1.00 | 1.45 | 22 |
| A + 6% Decane | ~0 | 50 | 93 | — | — | 1.30 | — | — | 22 |
| B | −2 | 81 | 108 | 31.66 | 24.23 | 0.65 | 1.10 | 1.50 | 22 |
| B + 6% Dihexyl ether | −2 | 64 | 66 | 28.92 | 20.45 | 2.37 | 0.90 | 1.35 | 22 |
| B + 4% Butyric acid propyl ester | −2 | 65 | 64 | — | — | — | 0.90 | 1.25 | 22 |
| C | ~0 | 82 | 119 | 32.77 | 25.65 | 0.52 | 1.10 | 1.60 | 22 |
| C + 7% p-xylene | ~0 | 60 | 62 | — | — | — | 0.90 | 1.40 | 22 |
| D | <0 | 84 | 57.5 | 21.10 | 16.03 | 2.5 | 1.70 | 2.35 | 22 |
| D + 6% Dihexyl ether | <0 | 67.5 | 44.0 | 18.54 | 13.07 | 6.2 | 1.42 | 1.90 | 22 |
| E | <0 | 99.5 | 114 | 27.83 | 21.06 | 0.46 | 1.55 | 2.10 | 22 |
| E + 15%① | <0 | 84.5 | 84.2 | 26.03 | 19.37 | 0.85 | 1.45 | 2.00 | 22 |
| E + 15%② | <0 | 81.0 | 72.1 | 25.05 | 18.87 | 0.91 | 1.50 | 2.05 | 22 |
| C + 15%③ | <0 | 62.0 | 66.0 | 28.69 | 21.92 | 1.40 | 1.20 | 1.70 | 22 |
| C + 15%② | <0 | 67.3 | 68.8 | 28.73 | 22.22 | 1.12 | 1.30 | 1.80 | 22 |
| F | | 65.0 | 84.0 | 26.00 | 18.3 | 0.62 | 1.40 | 1.90 | 22 |
| F + 15%④ | <0 | 55.7 | 61.6 | 24.53 | 16.99 | 1.48 | 1.25 | 1.70 | 22 |
| F + 15%① | <0 | 56.1 | 63.7 | 24.04 | 16.52 | 1.48 | 1.20 | 1.70 | 22 |
| B + 15%① | <0 | 70 | 76.0 | 29.38 | 22.09 | 1.08 | 1.25 | 1.70 | 22 |
| C + 5% Dihexyl ether + 8%② | <0 | 55 | 59.8 | 27.30 | 20.01 | 2.75 | 1.10 | 1.60 | 22 |

Table I-continued

| Mixture | M.p. (°C.) | C.p. (°C.) | Viscosity (cp) | $\epsilon_\mu$ | $\Delta\epsilon$ | fc (MHz) | V(10) (Volt) | V(90) (Volt) | Measuring temp. (°C.) |
|---|---|---|---|---|---|---|---|---|---|
| G + 10%① | <0 | 66 | 52 | 12.00 | 6.30 | — | 2.05 | 2.70 | 22 |

In Table I, the notations ①, ②, ③ and ④ have the following significance:
① 4'-Methylbenzylidene-4-n-butylaniline
② 4-n-Propyl-4'-n-pentylbiphenyl
③ 4-Ethyl-4'-n-butylbiphenyl
④ 4'-Methylbenzylidene-4-methylaniline.

In Table I, fc denotes the cross-over frequency, i.e., the frequency at which $\epsilon_\perp = \epsilon_\parallel$. V(10) and V(90) denote the threshold potential which was measured at 10% and 90% transmissivity of the display, respectively. The following nematogenic mixtures were used as mixtures A-G:

25% p-n-Butylbenzoic acid p'-cyanophenyl ester, 25% p-n-hexylbenzoic acid p'-cyanophenyl ester, 25% p-n-octylbenzoic acid p'-cyanophenyl ester and 25% methylhydroquinone di-p-n-butylbenzoate (mixture A).

7.7% p-n-Butylbenzoic acid p'-cyanophenyl ester, 8.1% p-n-butylbenzoic acid p'-cyanophenyl ester, 10.0% p-n-hexylbenzoic acid p'-cyanophenyl ester, 36.0% p-[(p-n-butylbenzylidene)-amino]benzonitrile, 8.4% 5-n-pentyl-2-(4-cyanophenyl)-pyrimidine, 15.8% 5-n-heptyl-2-(4-cyanophenyl)pyrimidine and 13.0% 2-(4-cyanophenyl)-5-(4-n-butylphenyl)pyrimidine (mixture B).

10.3% p-n-Butylbenzoic acid p'-cyanophenyl ester, 11.1% p-n-pentylbenzoic acid p'-cyanophenyl ester, 14.3% p-n-hexylbenzoic acid p'-cyanophenyl ester, 15.4% p-n-heptylbenzoic acid p'-cyanophenyl ester, 11.0% 5-n-pentyl-2-(4-cyanophenyl)-pyrimidine, 21.2% 5-n-heptyl-2-(4-cyanophenyl)pyrimidine and 15.6% 2-(4-cyanophenyl)-5-(4-n-butylphenyl)pyrimidine (mixture C).

46.8% 4'-n-Pentyl-4-cyanobiphenyl, 23.4% 4'-n-heptyl-4-cyanobiphenyl, 7.8% 4'-n-heptyloxy-4-cyanobiphenyl, 2.3% 2-(4-cyanophenyl)-5-(4-n-propylphenyl)pyrimidine, 11.3% 2-(4-cyanophenyl)-5-(4-n-butylphenyl)pyrimidine and 7.7% 4-cyano-4''-n-pentyl-p-terphenyl (mixture D).

10.3% p-[(p-n-Propylbenzylidene)-amino]benzonitrile, 29.3% p-[(p-n-butylbenzylidene)-amino]benzonitrile, 41.4% p-[(p-n-hexylbenzylidene)-amino]benzonitrile, 9.8% 2-(4-cyanophenyl)-5-(4-n-butylphenyl)-pyrimidine and 9.2% 5-n-butyl-2-(4'-cyano-4-biphenyl)-pyrimidine (mixture E).

2 Parts of p-[(p-n-hexylbenzylidene)-amino]benzonitrile and 1 part p-[(p-n-propylbenzylidene)-amino]benzonitrile (mixture F).

7% p-n-Butylbenzoic acid p'-cyanophenyl ester, 12.4% 2-(4-cyanophenyl)-5-(4-n-butylphenyl)pyrimidine, 56.1% 4'-methoxybenzylidene-4-n-butylaniline and 24.1% 4'-ethoxybenzylidene-4'-n-butylaniline (mixture G).

Exemplary of additional liquid crystal mixtures provided by the invention are the following:

10.3% p-n-Butylbenzoic acid p'-cyanophenyl ester, 11.1% p-n-pentylbenzoic acid p'-cyanophenyl ester, 14.3% p-n-hexylbenzoic acid p'-cyanophenyl ester, 15.4% p-n-heptylbenzoic acid p'-cyanophenyl ester, 11.0% 5-n-pentyl-2-(4-cyanophenyl)-pyrimidine, 21.2% 5-n-heptyl-2-(4-cyanophenyl)pyrimidine, 15.6% 2-(4-cyanophenyl)-5-(4-n-butylphenyl)pyrimidine and 15% 4-n-pentyl-4'-propylbiphenyl and 3% dihexyl ether; clearing point 56.2° C.

10.3% p-n-Butylbenzoic acid p'-cyanophenyl ester, 11.1% p-n-pentylbenzoic acid p'-cyanophenyl ester, 14.3% p-n-hexylbenzoic acid p'-cyanophenyl ester, 15.4% p-n-heptylbenzoic acid p'-cyanophenyl ester, 11.0% 5-n-pentyl-2-(4-cyanophenyl)-pyrimidine, 21.2% 5-n-heptyl-2-(4-cyanophenyl)pyrimidine, 15.6% 2-(4-cyanophenyl)-5-(4-n-butylphenyl)pyrimidine and 15% 4-ethyl-4'-n-butylbiphenyl and 3% dihexyl ether; clearing point 51.5° C.

10.3% p-n-Butylbenzoic acid p'-cyanophenyl ester, 11.1% p-n-pentylbenzoic acid p'-cyanophenyl ester, 14.3% p-n-hexylbenzoic acid p'-cyanophenyl ester, 15.4% p-n-heptylbenzoic acid p'-cyanophenyl ester, 11.0% 5-n-pentyl-2-(4-cyanophenyl)-pyrimidine, 21.2% 5-n-heptyl-2-(4-cyanophenyl)pyrimidine, 15.6% 2-(4-cyanophenyl)-5-(4-n-butylphenyl)pyrimidine and 15% 4-methyl-4'-n-pentylbiphenyl; clearing point 66.5° C.

10.3% p-n-Butylbenzoic acid p'-cyanophenyl ester, 11.1% p-n-pentylbenzoic acid p'-cyanophenyl ester, 14.3% p-n-hexylbenzoic acid p'-cyanophenyl ester, 15.4% p-n-heptylbenzoic acid p'-cyanophenyl ester, 11.0% 5-n-pentyl-2-(4-cyanophenyl)-pyrimidine, 21.2% 5-n-hexyl-2-(4-cyanophenyl)pyrimidine, 15.6% 2-(4-cyanophenyl)-5-(4-n-butylphenyl)pyrimidine and 15% 4-ethyl-4'-n-pentylbiphenyl; clearing point 64.9° C.

10.3% p-[(p-n-Propylbenzylidene)-amino]benzonitrile, 29.3% p-[(p-n-butylbenzylidene)-amino]benzonitrile, 41.4% p-[(p-n-hexylbenzylidene)-amino]benzonitrile, 9.8% 2-(4-cyanophenyl)-5-(4-n-butylphenyl)-pyrimidine, 9.2% 5-n-butyl-2-(4'-cyano-4-biphenyl)-pyrimidine and 15% 5-n-butyl-2-(4-ethylphenyl)-pyrimidine; clearing point 75° C.

2 Parts of p-[(p-n-hexylbenzylidene)-amino]benzonitrile and 1 part of p-[(p-n-propylbenzylidene)-amino]benzonitrile and 15% 4-ethyl-4'-n-pentylbiphenyl; clearing point 50.8° C.

2 Parts of p-[(p-n-hexylbenzylidene)-amino]benzonitrile and 1 part of p-[(p-n-propylbenzylidene)-amino]benzonitrile and 15% 4-ethyl-4'-n-propylbiphenyl; clearing point 50.5° C.

The Examples which follow further illustrate the preparation of the compounds of formulas VI, VII and (c). All temperatures are in degrees Centigrade and all parts are by weight, unless otherwise stated.

EXAMPLE 1

Preparation of 5-n-heptyl-2-(4-cyanophenyl)pyrimidine 1.9 G. of 4-(4-n-heptylpyrimid-2-yl)benzoic acid amide are refluxed for 80 minutes in a mixture of 40 ml. of ethylene chloride and 0.63 ml. of phosphorus oxychloride with stirring. The mixture, diluted with ether, is washed with 2-N sodium hydroxide solution and then with water until neutral. After evaporation of the organic phase, which has been dried over sodium sulfate, there are obtained 1.9 g. of 5-n-heptyl-2-(4-cyanophenyl)pyrimidine which are distilled in a high vacuum; melting point 44.2°–44.7° C.; clearing point 50.1°–50.4° C.

The starting material was prepared as follows:

0.07 Mol. of 2-n-heptyl-malonic tetraethyl acetal is stirred in 35 ml. of ethanol with 0.14 mol of water and 2 drops of concentrated sulfuric acid at 50° C. under an atmosphere of nitrogen for 15 hours. The acidic 2-heptyl-malonic aldehyde obtained as the by-product can be separated from the neutral 2-n-heptyl-3-ethoxy-acrolein by shaking out the mixture previously diluted with ether, with aqueous sodium carbonate solution.

A suspension of 0.1 mol of 4-amidino-benzoic acid ethyl ester hydrochloride, 0.1 mol of 2-n-heptyl-3-ethoxy-acrolein and 0.14 mol of sodium ethylate in 100 ml. of ethanol is stirred overnight at room temperature under an atmosphere of nitrogen. After the customary working-up and separation into basic and acidic portions, 4-(4-n-heptylpyrimid-2-yl)benzoic acid ethyl ester and 4-(4-n-heptylpyrimid-2-yl)benzoic acid are obtained.

A. 4.4 G. of 4-(4-n-heptylpyrimid-2-yl)benzoic acid ethyl ester dissolved in 50 ml. of methanol/dichloromethane (1:1) are treated with 30 ml. of liquid ammonia in a laboratory autoclave and the mixture is then warmed for 5 hours to 90° C. (pressure: 16 atmospheres absolute). The mixture is evaporated to dryness and the sparingly soluble amide is separated from unreacted educt, whereby 4-(4-n-heptylpyrimid-2-yl)benzoic acid amide is obtained.

B. 2.3 G. of 4-(4-n-heptylpyrimid-2-yl)benzoic acid and 1.9 ml. of thionyl chloride are left in 100 ml. of benzene for 8 hours at reflux and then the mixture is evaporated to dryness on a vacuum film evaporator. The resulting residue is dissolved in 50 ml. of dichloromethane and ammonia is passed into the solution at room temperature for 2 hours, whereby 4-(4-n-heptylpyrimid-2-yl)benzoic acid amide is obtained in virtually quantitative yield.

The following benzoic acid amides were prepared in an analogous manner:
4-(4-n-butylpyrimid-2-yl)benzoic acid amide,
4-(4-n-pentylpyrimid-2-yl)benzoic acid amide, and
4-(4-n-octylpyrimid-2-yl)benzoic acid amide.

EXAMPLE 2

Preparation of 5-n-pentyl-2-(4-cyanophenyl)pyrimidine 0.8 G. of 4-(4-n-pentylpyrimid-2-yl)benzoic acid amide is refluxed for 80 minutes in a mixture of 20 ml. of ethylene chloride and 0.35 ml. of phosphorus oxychloride with stirring. The mixture, diluted with ether, is washed with 2-N sodium hydroxide solution and then with water until neutral. After evaporation of the organic phase, which has been dried over sodium sulfate, there is obtained 0.82 g. of 5-n-pentyl-2-(4-cyanophenyl)pyrimidine which is distilled in a high vacuum; melting point 69.4°–70.8° C.; clearing point 51.9° C.

EXAMPLE 3

Preparation of 5-(4-n-butylphenyl)-2-(4-cyanophenyl)pyrimidine 102.75 G. of 4-[5-(4-n-butylphenyl)-2-pyrimidyl] benzoic acid amide are refluxed for 80 minutes in a mixture of 1500 ml. of ethylene chloride and 34 ml. of phosphorus oxychloride with stirring. The mixture, diluted with ether, is washed with 2-N sodium hydroxide solution and then with water until neutral. After evaporation of the organic phase, which has been dried over sodium sulfate, there is obtained 5-(4-n-butylphenyl)-2-(4-cyanophenyl)pyrimidine which is filtered on a short silica gel column and subsequently recrystallized from methylene chloride/methanol; melting point 94.7° C.; clearing point 246°–246.7° C.

The starting material can be prepared as follows:

Dry hydrochloric acid gas is passed into a solution of 88.6 g. of 4-cyanobenzoic acid methyl ester in 190 ml. of benzene and 70 ml. of methanol at 0° C. for 3 hours with stirring. The mixture is allowed to stand for 5 days at +5° C. and then the imido ether which has separated out is removed by filtration. 178 G. of this crude product are suspended in 300 ml. of methanol and, after cooling to about −40° C., treated with 130 g. of liquid ammonia and the mixture is shaken in an autoclave for 24 hours at +70° C. After cooling the reaction mixture to room temperature and allowing the ammonia to evaporate, the product which has crystallized out is removed by filtration. The crystals are washed with hexane and dried overnight at 50° C. under water-pump vacuum, and there is obtained 4-amidino-benzoic acid amide hydrochloride.

41.17 G. of 1-(4-n-butylphenyl)-2-methoxyethylene [preparation see Ber. 94, 1373 (1961)] are added dropwise to a solution of 0.315 ml. of boron trifluoride etherate in 99 ml. of orthoformic acid ethyl ester cooled in an ice-bath. The mixture is subsequently stirred at room temperature. After dilution with ether, extraction with 1-N sodium hydroxide solution and water and evaporation of the organic phase, which has been dried over sodium sulfate, there is obtained 4-n-butylphenyl-malonic tetraacetal.

158.7 G. of 4-n-butylphenyl-malonic tetraacetal are stirred overnight in 384 ml. of ethanol with 15 ml. of water and 25 drops of concentrated sulfuric acid at 50° C. under an atmosphere of nitrogen. The acidic butylphenyl-malonic aldehyde obtained as a by-product can be separated from the neutral 2-(4-n-butylphenyl)-3-ethoxy-acrolein by shaking out the mixture, diluted with ether, with aqueous sodium carbonate solution.

74.2 G. of 2-(4-n-butylphenyl)-3-ethoxy-acrolein, 77.8 g. of the 4-amidinobenzoic acid amide hydrochloride described earlier and 0.546 mol of sodium methylate (obtained by dissolving 12.55 g. of sodium metal in methanol) are suspended in 2500 ml. of methanol and stirred overnight at room temperature under an atmosphere of nitrogen. The yellow suspension is subsequently removed by filtration, washed with a small amount of ethanol and suspended in 4 liters of ether for further purification. The suspension is washed with water and then filtered again. Sparingly soluble 4-[5-(4-n-butylphenyl)-2-pyrimidinyl] benzoic acid amide is obtained.

The following compounds were prepared in an analogous manner:

| | Melting point | Clearing point |
|---|---|---|
| 5-(4-n-propylphenyl)-2-(4-cyanophenyl)pyrimidine | 154°–154.5° C. | 261° C. |
| 5-(4-n-hexylphenyl)-2-(4-cyanophenyl)pyrimidine | 93° C. | 232.5° C. |
| 5-(4-n-heptylphenyl)-2-(4-cyanophenyl)pyrimidine | 104.5° C. | 226° C. |

EXAMPLE 4

Preparation of 5-n-butyl-2-(4-ethylphenyl)pyrimidine 11.3 G. of 2-n-butyl-malonodialdehyde tetramethyl acetal in 23 ml. of ethanol and 1.9 ml. of water are treated with 5 drops of concentrated sulfuric acid and the mixture is stirred overnight at room temperature. The mixture is then taken up in ether and shaken with alkali. Finally, there are obtained 6.3 g. of 2-n-butyl-3-methoxyacrolein which is used without further purification.

6.3 G. of the crude 2-n-butyl-3-methoxy-acrolein obtained according to the preceding paragraph in 27 ml. of absolute methanol are added dropwise to 2.05 g. of sodium dissolved in 60 ml. of absolute methanol. 5.50 G. of p-ethylbenzamidine hydrochloride are added to the mixture and the resulting mixture is stirred at room temperature overnight. The mixture is then treated with methylene chloride, washed neutral with water, dried over sodium sulfate and concentrated. There are obtained 8.25 g. of crude product which are chromatographed on 700 g. of silica gel and subsequently distilled; boiling point 115°/0.2 mmHg.

We claim:

1. A nematic liquid crystal mixture having positive anisotropy of the dielectric constants which comprises a nematogenic mixture with a clearing point above 60° C. and one or more solvents individually selected from the group consisting of a straight-chain alkane of 8–16 carbon atoms, an alkyl halide of 6–16 carbon atoms, a dialkyl ether of 4–8 carbon atoms in each alkyl radical, a dialkyl carbonate of 2–7 carbon atoms in each alkyl radical, an alkanecarboxylic acid alkyl ester the alkyl radicals of which together contain 6–16 carbon atoms p-xylene, 1-phenylheptane, p-octylbenzoic acid methyl ester, and p-hexylbenzaldehyde.

2. A liquid crystal mixture, in accordance with claim 1, which contains 0.5% to 15% of solvent or solvent mixture.

3. A liquid crystal mixture, in accordance with claim 1, which contains 0.5% to 10% of solvent or solvent mixture.

4. A liquid crystal mixture, in accordance with claim 1, which contains 3% to 8% of solvent or solvent mixture.

5. A liquid crystal mixture, in accordance with claim 2, wherein the solvent is a dialkyl ether the alkyl radicals of which together contain 4–8 carbon atoms in each alkyl radical or an alkanecarboxylic acid alkyl ester of 6–16 carbon atoms.

6. A liquid crystal mixture, in accordance with claim 2, wherein the solvent is dibutyl ether, dihexyl ether, dioctyl ether, butyric acid propyl ester or butyric acid pentyl ester.

7. A liquid crystal mixture, in accordance with claim 1, in which the nematogenic mixture comprises two or more compounds selected from the group consisting of compounds of the formulas

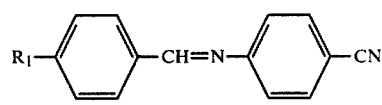

wherein $R_1$ is straight-chain alkyl containing 2 to 8 carbon atoms, straight-chain alkoxy containing 4 to 7 carbon atoms, straight-chain alkanoyloxy containing 2 to 8 carbon atoms or straight-chain alkylcarbonate containing 2 to 11 carbon atoms;

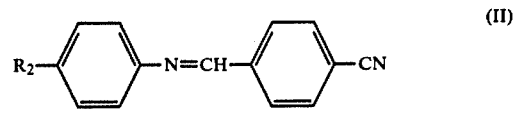

wherein $R_2$ is straight-chain alkyl containing 4 to 7 carbon atoms or straight-chain alkylcarbonate containing 2 to 11 carbon atoms;

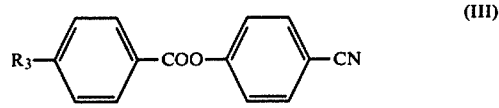

wherein $R_3$ is straight-chain alkyl containing 4 to 8 carbon atoms, straight-chain alkoxy containing 5 to 8 carbon atoms, straight-chain alkanoyloxy containing 2 to 8 carbon atoms or straight-chain alkylcarbonate containing 3 to 11 carbon atoms;

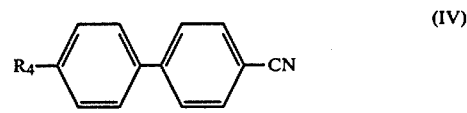

wherein $R_4$ is straight-chain alkyl containing 4 to 8 carbon atoms, straight-chain alkoxy containing 4 to 8 carbon atoms, straight-chain alkanoyloxy containing 4 to 9 carbon atoms or straight-chain alkylcarbonate containing 4 to 11 carbon atoms;

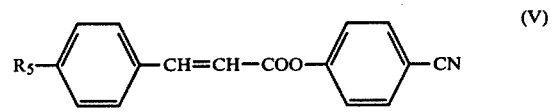

wherein $R_5$ is straight-chain alkyl containing 1 to 8 carbon atoms;

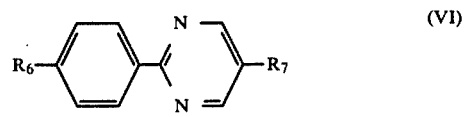

wherein one of $R_6$ and $R_7$ is cyano and the other is straight-chain alkyl containing 3 to 9 carbon atoms, straight-chain alkoxy containing 2 to 9 carbon atoms or straight-chain alkanoyloxy containing 2 to 9 carbon atoms;

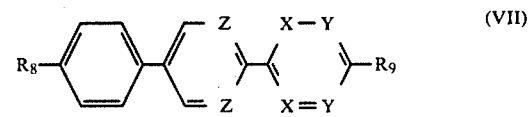

wherein one of $R_8$ and $R_9$ is hydrogen, straight-chain alkyl containing 1 to 7 carbon atoms, straight-chain alkoxy containing 1 to 7 carbon atoms or straight-chain alkanoyloxy containing 2 to 7 carbon atoms and the other is cyano and one of X, Y and Z is nitrogen and the other two are CH;

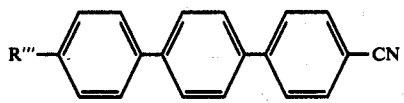

(B)

wherein R''' is straight-chain alkyl containing 3 to 8 carbon atoms.

8. A liquid crystal mixture, in accordance with claim 1, which consists of p-n-butylbenzoic acid p'-cyanophenyl ester, p-n-hexylbenzoic acid p'-cyanophenyl ester, p-n-octylbenzoic acid p'-cyanophenyl ester, methylhydroquinone di-p-n-butylbenzoate and dihexyl ether.

9. A liquid crystal mixture, in accordance with claim 1, which consists of 25% p-n-butylbenzoic acid p'-cyanophenyl ester, 25% p-n-hexylbenzoic acid p'-cyanophenyl ester, 25% p-n-octylbenzoic acid p'-cyanophenyl ester, 25% methylhydroquinone di-p-n-butylbenzoate and 6% dihexyl ether.

10. A liquid crystal mixture, in accordance with claim 1, which consists of p-n-butylbenzoic acid p'-cyanophenyl ester, p-n-hexylbenzoic acid p'-cyanophenyl ester, p-n-octylbenzoic acid p'-cyanophenyl ester, methylhydroquinone di-p-n-butylbenzoate and decane.

11. A liquid crystal mixture, in accordance with claim 1, which consists of 25% p-n-butylbenzoic acid p'-cyanophenyl ester, 25% p-n-hexylbenzoic acid p'-cyanophenyl ester, 25% p-n-octylbenzoic acid p'-cyanophenyl ester, 25% methylhydroquinone di-p-n-butylbenzoate and 6% decane.

12. A liquid crystal mixture, in accordance with claim 1, which consists of p-n-butylbenzoic acid p'-cyanophenyl ester, p-n-pentylbenzoic acid p'-cyanophenyl ester, p-n-hexylbenzoic acid p'-cyanophenyl ester, p-[(p-n-butylbenzylidene)-amino] benzonitrile, 5-n-pentyl-2-(4-cyanophenyl)pyrimidine, 5-n-heptyl-2-(4-cyanophenyl)pyrimidine, 2-(4-cyanophenyl)-5-(4-n-butylphenyl)pyrimidine and dihexyl ether.

13. A liquid crystal mixture, in accordance with claim 1, which consists of 7.7% p-n-butylbenzoic acid p'-cyanophenyl ester, 8.1% p-n-pentylbenzoic acid p'-cyanophenyl ester, 10.0% p-n-hexylbenzoic acid p'-cyanophenyl ester, 36.0% p-[(p-n-butylbenzylidene)-amino]-benzonitrile, 8.4% 5-n-pentyl-2-(4-cyanophenyl)-pyrimidine, 15.8% 5-n-heptyl-2-(4-cyanophenyl)pyrimidine, 13.0% 2-(4-cyanophenyl)-5-(4-n-butylphenyl)pyrimidine and 6% dihexyl ether.

14. A liquid crystal mixture, in accordance with claim 1, which consists of p-n-butylbenzoic acid p'-cyanophenyl ester, p-n-pentylbenzoic acid p'-cyanophenyl ester, p-n-hexylbenzoic acid p'-cyanophenyl ester, p-[(p-n-butylbenzylidene)-amino]benzonitrile, 5-n-pentyl-2-(4-cyanophenyl)pyrimidine, 5-n-heptyl-2-(4-cyanophenyl)-pyrimidine, 2-(4-cyanophenyl)-5-(4-n-butylphenyl)pyrimidine and butyric acid propyl ester.

15. A liquid crystal mixture, in accordance with claim 1, which consists of 7.7% p-n-butylbenzoic acid p'-cyanophenyl ester, 8.1% p-n-pentylbenzoic acid p'-cyanophenyl ester, 10.0% p-n-hexylbenzoic acid p'-cyanophenyl ester, 36% p-[(p-n-butylbenzylidene)amino]-benzonitrile, 8.4% 5-n-pentyl-2-(4-cyanophenyl)pyrimidine, 15.8% 5-n-heptyl-2-(4-cyanophenyl)pyrimidine, 13.0% 2-(4-cyanophenyl)-5-(4-n-butylphenyl)pyrimidine and 4% butyric acid propyl ester.

16. A liquid crystal mixture, in accordance with claim 1, which consists of p-n-butylbenzoic acid p'-cyanophenyl ester, p-n-pentylbenzoic acid p'-cyanophenyl ester, p-n-hexylbenzoic acid p'-cyanophenyl ester, p-n-heptylbenzoic acid p'-cyanophenyl ester, 5-n-pentyl-2-(4-cyanophenyl)pyrimidine, 5-n-heptyl-2-(4-cyanophenyl)pyrimidine, 2-(4-cyanophenyl)-5-(4-n-butylphenyl)pyrimidine and p-xylene.

17. A liquid crystal mixture, in accordance with claim 1, which consists of 10.3% p-n-butylbenzoic acid p'-cyanophenyl ester, 11.1% p-n-pentylbenzoic acid p'-cyanophenyl ester, 14.3% p-n-hexylbenzoic acid p'-cyanophenyl ester, 15.4% p-n-heptylbenzoic acid p'-cyanophenyl ester, 11.0% 5-n-pentyl-2-(4-cyanophenyl)pyrimidine, 21.2% 5-n-heptyl-2-(4-cyanophenyl)pyrimidine, 15.6% 2-(4-cyanophenyl)-5-(4-n-butylphenyl)pyrimidine and 7% p-xylene.

18. A liquid crystal mixture, in accordance with claim 1, which consists of 4'-n-pentyl-4-cyanobiphenyl, 4'-n-heptyl-4-cyanobiphenyl, 4'-heptyloxy-4-cyanobiphenyl, 2-(4-cyanophenyl)-5-(4-n-propylphenyl)pyrimidine, 2-(4-cyanophenyl)-5-(4-n-butylphenyl)-pyrimidine, 4-cyano-4''-n-pentyl-p-terphenyl and dihexyl ether.

19. A liquid crystal mixture, in accordance with claim 1, which consists of 46.8% 4'-n-pentyl-4-cyanobiphenyl, 23.4% 4'-n-heptyl-4-cyanobiphenyl, 7.8% 4'-n-heptyloxy-4-cyanobiphenyl, 2.3% 2-(4-cyanophenyl)-5-(4-n-propylphenyl)pyrimidine, 11.3% 2-(4-cyanophenyl)-5-(4-n-butylphenyl)pyrimidine, 7.7% 4-cyano-4''-n-pentyl-p-terphenyl and 6% dihexyl ether.

20. A nematic liquid crystal mixture having positive anisotropy of the dielectric constants which comprises a nematogenic mixture with a clearing point above 60° C. and one or more solvents individually selected from the group consisting of a straight-chain alkane of 8–16 carbon atoms, an alkyl halide of 6–16 carbon atoms, a dialkyl ether of 4–8 carbon atoms in each alkyl radical, a dialkyl carbonate of 2–7 carbon atoms in each alkyl radical, an alkanecarboxylic acid alkyl ester the alkyl radicals of which together contain 6–16 carbon atoms, p-xylene, 1-phenylheptane, p-octylbenzoic acid methyl ester, p-hexylbenzaldehyde, and a compound of the formula

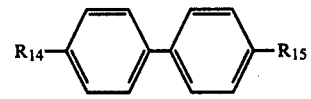

(a)

wherein $R_{14}$ and $R_{15}$ are straight-chain alkyl containing, together, a total of not more than 14 carbon atoms or $R_{14}$ is straight-chain alkyl and $R_{15}$ is straight-chain alkoxy containing, together, a total of not more than 8 carbon atoms, provided said nematogenic mixture contains at least one compound selected from the formula

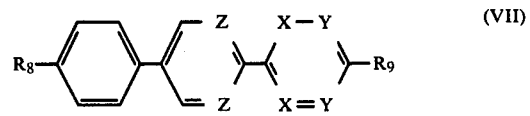

(VII)

wherein one of $R_8$ and $R_9$ is hydrogen, straight-chain alkyl containing 1 to 7 carbon atoms, straight-chain alkoxy containing 1 to 7 carbon atoms or straight-chain alkanoyloxy containing 2 to 7 carbon atoms and the other is cyano and one of X, Y and Z is nitrogen and the other two are CH.

21. A nematic liquid crystal mixture, in accordance with claim 20, in which the nematogenic mixture comprises two or more compounds selected from the group consisting of compounds of the formulas

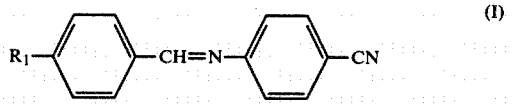

(I)

wherein $R_1$ is straight-chain alkyl containing 2 to 8 carbon atoms, straight-chain alkoxy containing 4 to 7 carbon atoms, straight-chain alkanoyloxy containing 2 to 8 carbon atoms or straight-chain alkylcarbonate containing 2 to 11 carbon atoms;

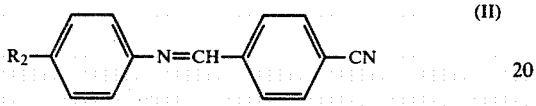

(II)

wherein $R_2$ is straight-chain alkyl containing 4 to 7 carbon atoms or straight-chain alkylcarbonate containing 2 to 11 carbon atoms;

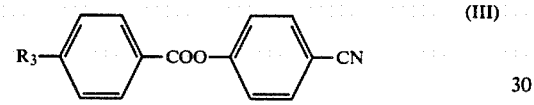

(III)

wherein $R_3$ is straight-chain alkyl containing 4 to 8 carbon atoms, straight-chain alkoxy containing 5 to 8 carbon atoms, straight-chain alkanoyloxy containing 2 to 8 carbon atoms or straight-chain alkylcarbonate containing 3 to 11 carbon atoms;

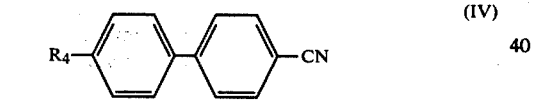

(IV)

wherein $R_4$ is straight-chain alkyl containing 4 to 8 carbon atoms, straight-chain alkoxy containing 4 to 8 carbon atoms, straight-chain alkanoyloxy containing 4 to 9 carbon atoms or straight-chain alkylcarbonate containing 4 to 11 carbon atoms;

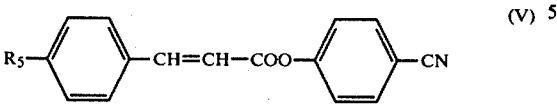

(V)

wherein $R_5$ is straight-chain alkyl containing 1 to 8 carbon atoms;

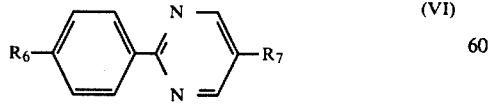

(VI)

wherein one of $R_6$ and $R_7$ is cyano and the other is straight-chain alkyl containing 3 to 9 carbon atoms, straight-chain alkoxy containing 2 to 9 carbon atoms or straight-chain alkanoyloxy containing 2 to 9 carbon atoms;

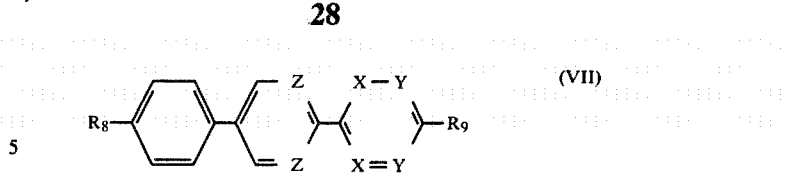

(VII)

wherein one of $R_8$ and $R_9$ is hydrogen, straight-chain alkyl containing 1 to 7 carbon atoms, straight-chain alkoxy containing 1 to 7 carbon atoms or straight-chain alkanoyloxy containing 2 to 7 carbon atoms and the other is cyano and one of X, Y and Z is nitrogen and the other two are CH; and

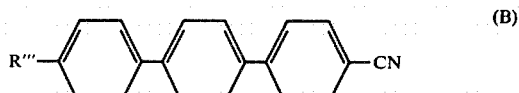

(B)

wherein $R'''$ is straight-chain alkyl containing 3 to 8 carbon atoms, provided said nematogenic mixture contains at least one compound selected from the formula

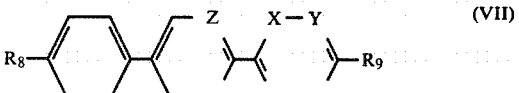

(VII)

wherein one of $R_8$ and $R_9$ is hydrogen, straight-chain alkyl containing 1 to 7 carbon atoms, straight-chain alkoxy containing 1 to 7 carbon atoms or straight-chain alkanoyloxy containing 2 to 7 carbon atoms and the other is cyano and one of X, Y and Z is nitrogen and the other two are CH.

22. A liquid crystal mixture, in accordance with claim 20, p-n-butylbenzoic acid p'-cyanophenyl ester, p-n-pentylbenzoic acid p'-cyanophenyl ester, p-n-hexylbenzoic acid p'-cyanophenyl ester, p-n-heptylbenzoic acid p'-cyanophenyl ester, 5-n-pentyl-2-(4-cyanophenyl)-pyrimidine, 5-n-heptyl-2-(4-cyanophenyl)pyrimidine, 2-(4-cyanophenyl)-5-(4-n-butylphenyl)pyrimidine and 4-ethyl-4'-n-butylbiphenyl and dihexyl ether.

23. A liquid crystal mixture, in accordance with claim 20, 10.3% p-n-butylbenzoic acid p'-cyanophenyl ester, 11.1% p-n-pentylbenzoic acid p'-cyanophenyl ester, 14.3% p-n-hexylbenzoic acid p'-cyanophenyl ester, 15.4% p-n-heptylbenzoic acid p'-cyanophenyl ester, 11.0% 5-n-pentyl-2-(4-cyanophenyl)pyrimidine, 21.2% 5-n-heptyl-2-(4-cyanophenyl)pyrimidine, 15.6% 2-(4-cyanophenyl)-5-(4-n-butylphenyl)pyrimidine and 15% 4-ethyl-4'-n-butylbiphenyl and 3% dihexyl ether.

24. A liquid crystal mixture, in accordance with claim 20, p-n-butylbenzoic acid p'-cyanophenyl ester, p-n-pentylbenzoic acid p'-cyanophenyl ester, p-n-hexylbenzoic acid p'-cyanophenyl ester, p-n-heptylbenzoic acid p'-cyanophenyl ester, 5-n-pentyl-2-(4-cyanophenyl)-pyrimidine, 5-n-heptyl-2-(4-cyanophenyl)pyrimidine, 2-(4-cyanophenyl)-5-(4-n-butylphenyl)pyrimidine and 4-methyl-4'-n-pentylbiphenyl.

25. A liquid crystal mixture, in accordance with claim 20, 10.3% p-n-butylbenzoic acid p'-cyanophenyl ester, 11.1% p-n-pentylbenzoic acid p'-cyanophenyl ester, 14.3% p-n-hexylbenzoic acid p'-cyanophenyl ester, 15.4% p-n-heptylbenzoic acid p'-cyanophenyl ester, 11.0% 5-n-pentyl-2-(4-cyanophenyl)pyrimidine, 21.2% 5-n-heptyl-2-(4-cyanophenyl)pyrimidine, 15.6% 2-(4- cyanophenyl)-5-(4-n-butylphenyl)pyrimidine and 15% 4-methyl-4'-n-pentylbiphenyl.

26. A liquid crystal mixture, in accordance with claim 20, p-n-butylbenzoic acid p'-cyanophenyl ester, p-n-pentylbenzoic acid p'-cyanophenyl ester, p-n-hexylbenzoic acid p'-cyanophenyl ester, p-n-heptylbenzoic acid p'-cyanophenyl ester, 5-n-pentyl-2-(4-cyanophenyl)pyrimidine, 5-n-hexyl-2-(4-cyanophenyl)pyrimidine, 2-(4-cyanophenyl)-5-(4-n-butylphenyl)pyrimidine and 4-ethyl-4'-n-pentylbiphenyl.

27. A liquid crystal mixture, in accordance with claim 20, 10.3% p-n-butylbenzoic acid p'-cyanophenyl ester, 11.1% p-n-pentylbenzoic acid p'-cyanophenyl ester, 14.3% p-n-hexylbenzoic acid p'-cyanophenyl ester, 15.4% p-n-heptylbenzoic acid p'-cyanophenyl ester, 11.0% 5-n-pentyl-2-(4-cyanophenyl)pyrimidine, 21.2% 5-n-hexyl-2-(4-cyanophenyl)pyrimidine, 15.6% 2-(4-cyanophenyl)-5-(4-n-butylphenyl)pyrimidine and 15% 4-ethyl-4'-n-pentylbiphenyl.

* * * * *